(12) United States Patent
Namerikawa et al.

(10) Patent No.: US 6,231,811 B1
(45) Date of Patent: *May 15, 2001

(54) CERAMIC SUBSTRATE AND SENSOR ELEMENT USING THE CERAMIC SUBSTRATE

(75) Inventors: Masahiko Namerikawa, Inazawa; Kazuyoshi Shibata, Mizunami, both of (JP)

(73) Assignee: NGK Insulators, Ltd., Nagoya (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/116,742

(22) Filed: Jul. 16, 1998

(30) Foreign Application Priority Data

Jul. 18, 1997 (JP) .................................................. 9-193934

(51) Int. Cl.⁷ ...................................................... G01N 29/02
(52) U.S. Cl. ........................ 422/68.1; 73/54.24; 310/328; 422/56; 422/82.01
(58) Field of Search .................... 422/68.1, 56, 82.01; 73/54.24, 54.25; 310/328, 339, 338

(56) References Cited

U.S. PATENT DOCUMENTS

| | | | |
|---|---|---|---|
| 4,892,794 | * | 1/1990 | Scholz . |
| 5,489,465 | * | 2/1996 | Natarajan et al. .................... 428/210 |
| 5,622,871 | * | 4/1997 | May et al. ............................ 436/514 |
| 5,698,931 | * | 12/1997 | Shibata et al. ....................... 310/338 |
| 5,889,351 | * | 3/1999 | Okumura et al. .................... 310/321 |
| 5,892,143 | * | 4/2000 | Namerikawa et al. ............. 73/54.24 |
| 5,933,170 | * | 8/1999 | Takeuchi et al. ....................... 347/71 |

FOREIGN PATENT DOCUMENTS

0409250936A * 9/1997 (JP) .

* cited by examiner

Primary Examiner—Arlin Soderquist
(74) Attorney, Agent, or Firm—Burr & Brown

(57) ABSTRACT

A ceramic substrate and a sensor element using the ceramic substrate. The ceramic substrate has a flat substrate in which an envelopment space is formed and a porous body disposed so as to cover the envelopment space. The porous body has flexibility and contact-bonding means is set to contact-bond the porous body with the flat substrate in the laminate direction. The porous body is constituted by using a woven fabric or non-woven fabric made of any one of natural fiber, synthetic fiber, and inorganic fiber so that the thickness $t_0$ of the porous body before contact-bonded and the thickness $t$ of the porous body 11 after contact-bonded meet the relation of $0.1 t_0 \leq t < t_0$. The porous body is provided with an overhanging portion to the outside of the flat substrate. The ceramic substrate prevents a fluid in the envelopment space from being replaced with bubbles even when the fluid is not sufficiently present nearby the envelopment space and there are a lot of bubbles.

12 Claims, 14 Drawing Sheets

CERAMIC SUBSTRATE AND SENSOR ELEMENT USING THE CERAMIC SUBSTRATE

BACKGROUND OF THE INVENTION AND RELATED ART STATEMENT

The present invention relates to a sensor element carrying a piezoelectric element and a ceramic substrate with an envelopment space formed in it preferably used for the sensor element.

A sensor element carrying a piezoelectric element or the like is used for measurement of the viscosity of a fluid, detection of solid particles in a fluid, and detection of vibrations.

For example, a sensor element is disclosed (official gazette of Japanese Patent Laid-Open No. 8-201265) which measures the viscosity of a fluid by using the characteristic of a piezoelectric film or vibrational portion (hereafter referred to as piezoelectric film or the like) that the amplitude of the piezoelectric film or the like decreases when the piezoelectric film or the like contacts a fluid to be measured (hereafter referred to as fluid) and the fluid has a large viscosity and increases when it has a small viscosity and thereby, applying a voltage to the piezoelectric film to detect a current corresponding to amplitude or the like, and measuring the changes of loss factors, electric resistances, and reactances of the piezoelectric film.

In the case of the sensor element, when the viscosity of a fluid such as a sulfuric-acid solution has a correlation with the specific gravity or component concentration of the fluid, it is possible to measure the specific gravity or component concentration of the fluid. Therefore, for example, it is possible to measure the change of specific gravities of sulfuric acid used as the electrolyte of a lead acid battery in accordance with the change of viscosities of the sulfuric acid and obtain the charge or discharge state of the battery.

FIG. 2 shows an example of the state in which the sensor element 1 is set in a lead acid battery. A porous separator 14 is inserted between a pair of electrodes 13a and 13b of the lead acid battery and the sensor element 1 is held so as to be embedded in the separator 14.

By storing the sensor element 1 in a battery case and injecting an electrolyte into a liquid case under the state, it is possible to measure the viscosity of the electrolyte because the electrolyte permeates the separator 14 and the gap between the electrodes 13a and 13b is filled with the electrolyte, and the electrolyte leaking out of the gap enters an envelopment space 6 through communication holes 15a and 15b formed on a flat substrate 2 and contacts led a vibrational portion 8.

In the case of the sensor element, however, if a fluid to be measured is a fluid having a large viscosity such as an aqueous solution or sulfuric acid or a fluid having a low wettability with the ceramics forming the flat substrate, or the envelopment space of the flat substrate is communicated with the outside of the substrate through a small communication hole, a difficult problem occurs that the air in the envelopment space of the flat substrate is not easily replaced with the fluid.

Moreover, there is a problem that even after a fluid to be measured is sufficiently supplied into the envelopment space, a sufficient amount of fluid is not present nearby the envelopment space or even if the fluid is sufficiently present, the fluid once supplied is replaced with bubbles again when many bubbles are present.

SUMMARY OF THE INVENTION

The present invention is made to solve the above conventional problems and its object is to prevent a fluid in an envelopment space from being replaced with bubbles again even when the fluid is not sufficiently present nearby the envelopment space and many bubbles are present.

That is, the present invention provides a ceramic substrate comprising a flat substrate with an envelopment space formed in it and a flexible porous body disposed so as to cover the envelopment space, and contact-bonding means for contact-bonding the porous body to the flat substrate in a laminate direction.

In the case of a ceramic substrate of the present invention, it is preferable that the relation of $0.1t_0 \leq t < t_0$ is satisfied when assuming the thickness of the porous body contact-bonded by the contact-bonding means with the flat substrate in the laminate direction as t and the thickness of the porous body before contact-bonded as $t_0$. Preferably, the porous body is formed from a woven fabric or non-woven fabric made of any one of natural fiber, synthetic fiber, and inorganic formed from envelopment space communicates with an external space preferably through at least two communication holes formed in the flat substrate, and the porous body is disposed so as to cover all of the two or more communication holes.

Moreover, in the case of the ceramic substrate of the present invention, it is preferable that the contact-bonding means has a window for making the porous body face-contact with a fluid, the porous body is sealed by the contact-bonding means, and moreover the window is formed on a portion of the contact-bonding means other than the portion of it for directly contact-bonding the porous body over the communication hole.

Moreover, it is preferable that the porous body has an overhanging portion to the outside of the flat substrate. In this case, it is more preferable that one end of the overhanging portion in the longitudinal direction contacts a fluid and the other end of it contacts a fluid absorbent.

Furthermore, it is preferable that the flat substrate at a portion contacting at least the porous body has a surface roughness of 50 μm or less.

Furthermore, the present invention provides a sensor element comprising a substrate having a vibrational portion and a piezoelectric element having a piezoelectric film and a pair of electrodes secured to one surface of the vibrational portion and contacting the piezoelectric film, in which the other surface of the vibrational portion serves as a sensor element facing an envelopment space and the substrate uses the ceramic substrate of the present invention.

In the case of the sensor element of the present invention, it is preferable that the envelopment space and the hole of the porous body disposed so as to cover the envelopment space are filled with at least one selected from the group consisting of a solid soluble in a fluid, a high-viscosity liquid soluble in a fluid, a solid reactive on a fluid, and a high-viscosity liquid reactive on a fluid, and it is more preferable that the at least one selected from the group consisting of a solid soluble in a fluid, a highviscosity viscosity liquid soluble in a fluid, a solid reactive on a fluid, and a high-viscosity liquid reactive on a fluid is replaced with a fluid.

BRIEF DESCRIPTION OF THE DRAWINGS

FIGS. 1(a) to 1(d) show an embodiment of a ceramic substrate of the present invention, in which FIG. 1(a) is a schematic perspective view of the embodiment, FIG. 1(b) is a sectional view of the embodiment, taken along the line B–B' in FIG. 1(a), FIG. 1(c) is a sectional view of the embodiment, taken along the line A–A' in FIG. 1(a), and FIG. 1(d) is a bottom view of the embodiment in FIG. 1(a).

FIGS. 5(a) to 5(d) show another embodiment of the ceramic substrate of the present invention in FIG. 1, in which FIG. 5(a) is a schematic perspective view of the embodiment, FIG. 5(b) is a sectional view of the embodiment, taken along the line B–B' in FIG. 5(a), FIG. 5(c) is a sectional view of the embodiment, taken along the line A–A' in FIG. 5(a), and FIG. 5(d) is a bottom view of the embodiment in FIG. 5(a).

FIGS. 6(a) to 6(c) show an embodiment of a ceramic substrate of the present invention, in which FIG. 6(a) is a schematic perspective view of the embodiment, FIG. 6(b) is a sectional view of the embodiment under a working state, taken along the line B–B' in FIG. 6(a), and FIG. 6(c) is a front view of the embodiment under a working state.

FIGS. 7(a) to 7(d) show an embodiment of a ceramic substrate of the present invention, in which FIG. 7(a) is a schematic perspective view of the embodiment, FIG. 7(b) is a sectional view of the embodiment, taken along the line A–A' in FIG. 7(a), FIG. 7(c) is a sectional view of the embodiment, taken along the line B–B' in FIG. 15 7(a), and FIG. 7(d) is a bottom view of the embodiment.

FIGS. 10(a) to 10(c) show an embodiment of a ceramic substrate of the present invention, in which FIG. 10(a) is a schematic perspective view of the embodiment, FIG. 10(b) is a sectional view of the embodiment under a working state, taken along the line A–A' in FIG. 10(a), and FIG. 10(c) is a sectional view of the embodiment under working state, taken along the line B–B' in FIG. 10(a).

DETAILED DESCRIPTION OF PREFERRED EMBODIMENT

Because the present invention relates to a ceramic substrate and a sensor element using the ceramic substrate, the whole of the sensor element is first described below by referring to the accompanying drawings.

Figure 3:
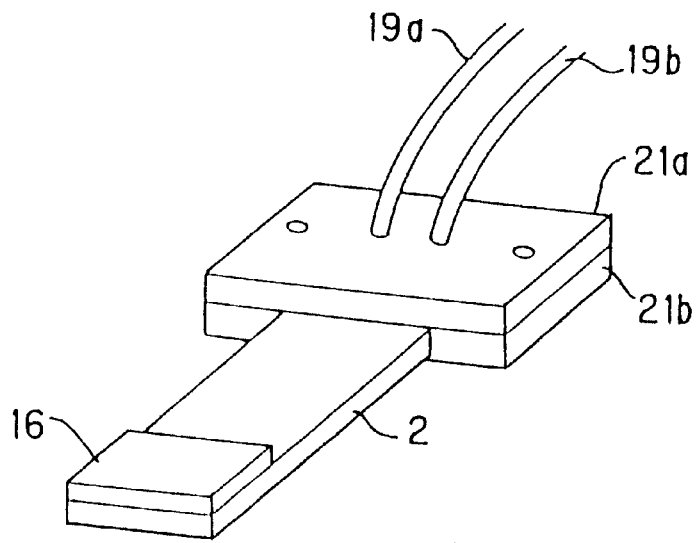
FIG. 3(a) is a schematic perspective view of a sensor element and FIG. 3(b) is an exploded perspective view of the sensor element in FIG. 3(a).
Figure 3:
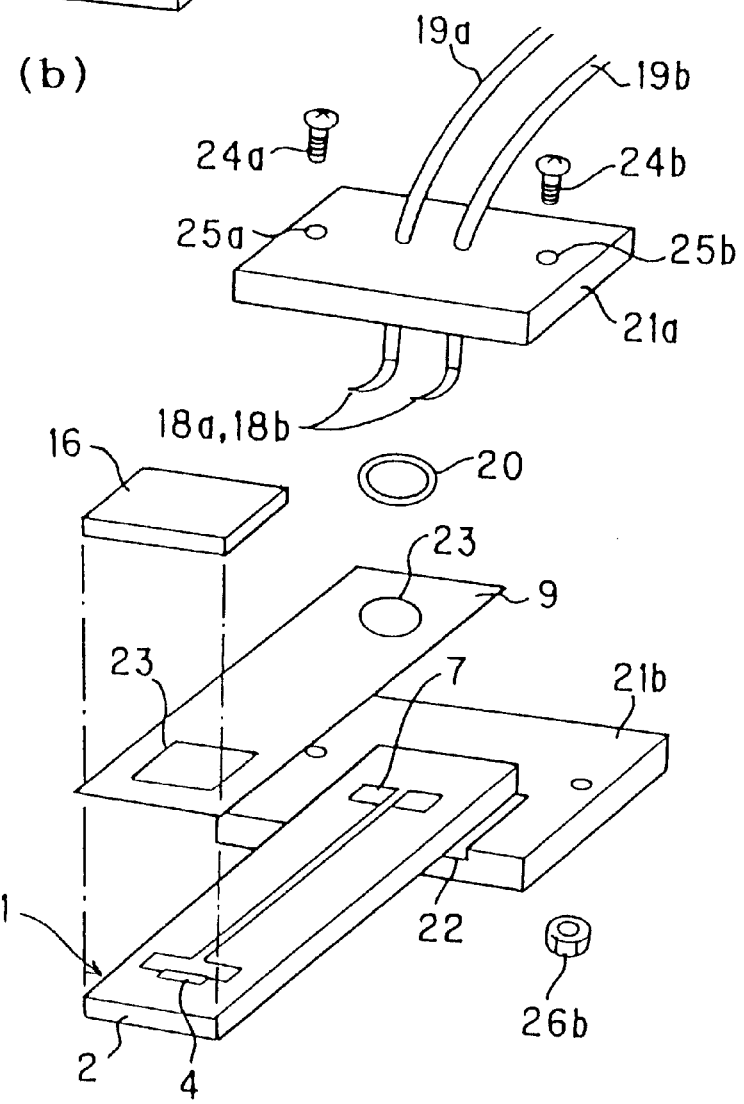
Figure 4:
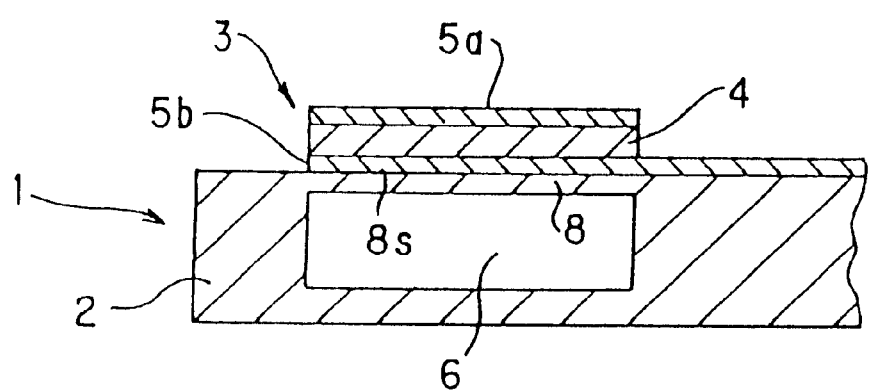
FIG. 4 is a sectional illustration showing a detailed structure of a sensor element.

A sensor element 1 used for the present invention has a general structure shown in, for example, FIGS. 3(a), 3(b) and 4. As its detailed structure, the sensor element 1 has a flat substrate 2 having a vibrational portion 8 and a piezoelectric element 3 secured to a vibrational-portion surface 8s as shown in FIG. 4 and an envelopment space 6 is formed in the flat substrate 2 so that the wall thickness of the vibrational portion 8 decreases.

Moreover, though not illustrated, the envelopment space 6 is constituted by a communication hole formed at a part of the back of the flat substrate 2 so that it communicates with an external space.

Furthermore, the piezoelectric element 3 has a piezoelectric film 4 and a pair of electrodes 5a and 5b for holding the piezoelectric film 4 and an electrode terminal 7 electrically connecting with the electrodes 5a and 5b is formed on the surface of the flat substrate 2.

In the case of the sensor element 1, a fluid to be measured is introduced into the envelopment space 6 through a communication hole and the viscosity or the like of the fluid can be measured by vibrating the vibrational portion 8.

In FIG. 3, symbol 9 denotes a piezoelectric-element protective layer, 16 denotes a cover, 18a and 18b denote a flat-spring-shaped terminals, 19a and 19b denote lead wires, 20 denotes an O-ring, 21a and 21b denote keep plates, 22 denotes a recess, 23 denotes a hollowed portion, 24a and 24b denote bolts, 25a and 25b denote holes, and 26b denotes a nut.

A ceramic substrate of the present invention comprises a flat substrate in which an envelopment space is formed and a porous body disposed so as to cover the envelopment space, in which the porous body has flexibility and contact-bonding means for contact-bonding the porous body to the flat substrate in the laminate direction.

By contact-bonding the porous body with the flat substrate by the contact-bonding means, gaps are not easily formed between the flat substrate (hereafter referred to as substrate) and the porous body differently from the case of only contacting the porous body with the flat substrate. Therefore, even if a fluid is not sufficiently present nearby the substrate or a lot of bubbles are present, it is possible to prevent the fluid in the envelopment space from being replaced with the bubbles again.

In the case of the present invention, an envelopment space represents a space formed in a flat substrate by including a vibrational portion serving as a detection portion of a sensor and the viscosity or the like of a fluid can be measured when the fluid is introduced into the envelopment space.

Though one face of the envelopment space can be opened to an external space, it is preferable to communicate the envelopment space with the external space only by at least two communication holes in order to decrease the contact area between a porous body and the envelopment space and decrease the probability for a gap to be produced between the porous body and the envelopment space, and it is more preferable that the porous body is disposed so as to cover all of the two or more communication holes in order to prevent bubbles or the like from entering the envelopment space through a communication hole.

A porous body used for the present invention uses a woven fabric or nonwoven fabric made of a material having flexibility such as natural fiber, synthetic fiber, or inorganic fiber.

A porous body having flexibility is increased in adhesiveness with a substrate by contact-bonding the porous body to a substrate by pressurizing it and thereby, gaps are not easily produced. Therefore, it is possible to prevent a fluid in an envelopment space from being replaced with bubbles and moreover prevent the substrate from being damaged by absorbing pressure.

When a porous body constituted with fiber such as a woven fabric or nonwoven fabric is wet by a fluid, it is contracted due to the capillary force between fibers. Therefore, a gap is easily produced on the interface between the porous body and a substrate when the porous body is only put on the substrate. However, by contact-bonding the porous body to the substrate by pressurizing it as in the present invention, the above problem does not occur.

Moreover, it is impossible to use a material having rigidity and non-flexibility such as ceramics even as a porous body. This is because the adhesiveness with a substrate cannot be secured or a pressure cannot be absorbed.

In the case of a ceramic substrate of the present invention, it is preferable to meet the relation of $0.1t_0 \leq t < t_0$ when assuming the thickness of a porous body contact-bonded by contact-bonding means in the laminate direction with a flat substrate as t and the thickness of the porous body before contact-bonding as $t_0$.

When the thickness of the porous body exceeds the above range, the pressure working between the substrate and the porous body decreases. Therefore, a gap is more easily produced between the substrate and the porous body. However, when the thickness becomes smaller than the above range, the pressure increases and therefore, the substrate may be broken.

Because the substrate strength fluctuates, it is more preferable to meet the relation of $0.2t_0 \leq t \leq 0.9t_0$ and it is particularly preferable to meet the relation of $0.3t_0 \leq t \leq 0.8t_0$ in order to secure the above effect.

Moreover, it is possible to set the thickness of a porous body in accordance with the load for bonding or the rigidity of contact-bonding means.

Figure 1:
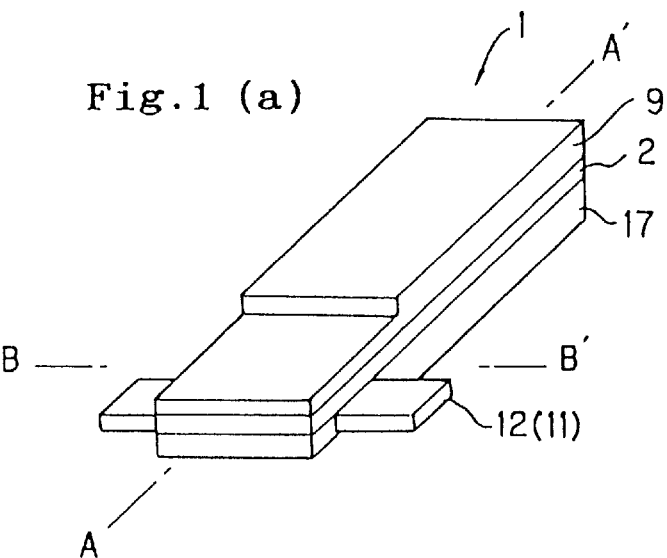
Figure 1:
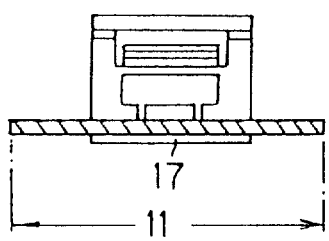
Figure 1:
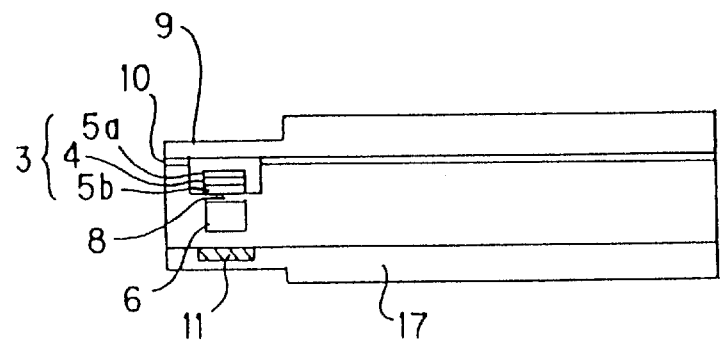
Figure 1:
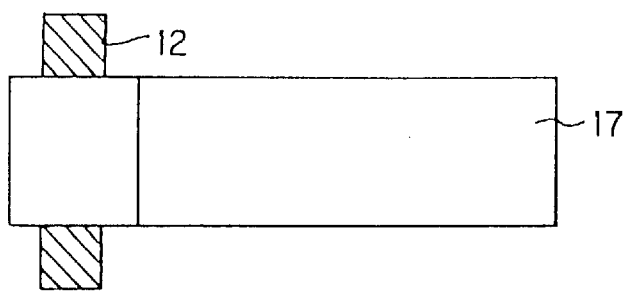
Figure 2:
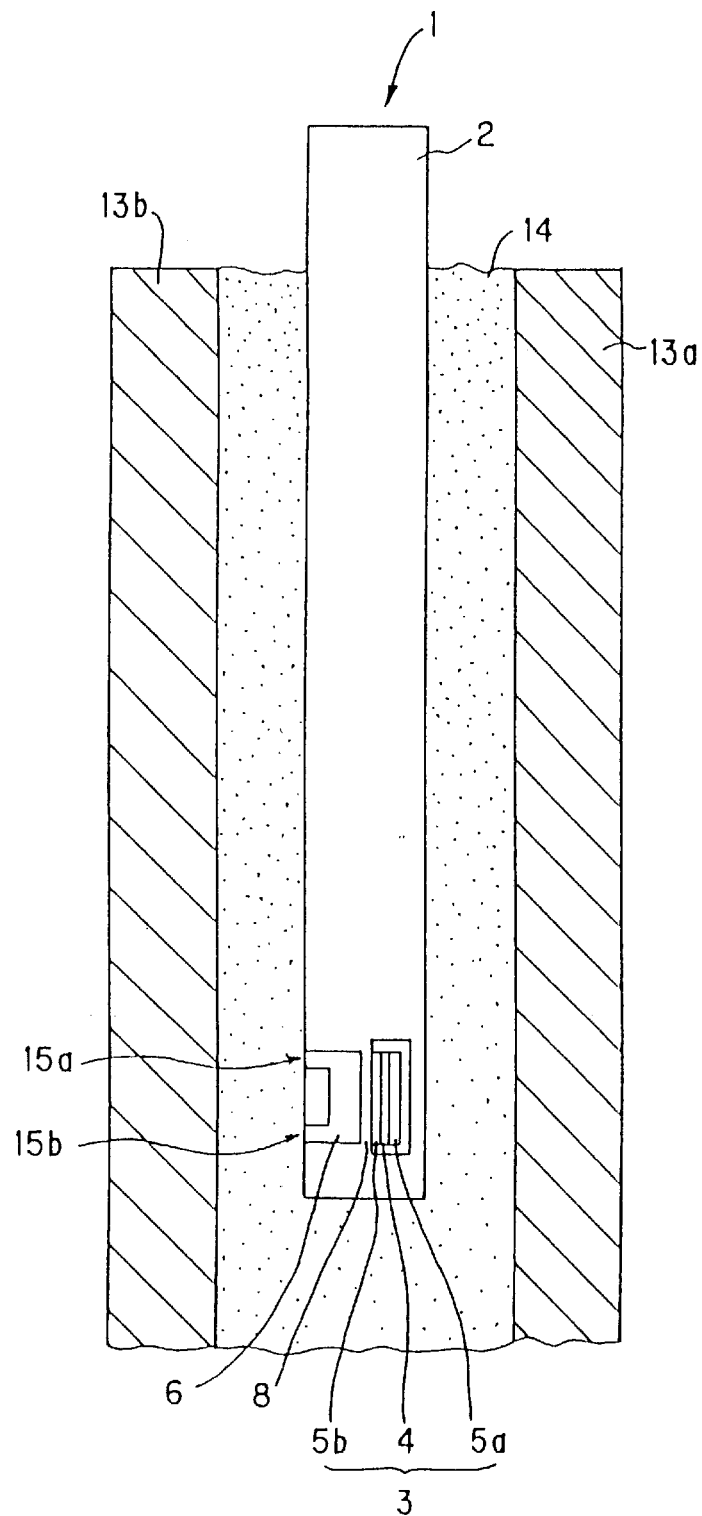
FIG. 2 is a lateral sectional view of a conventional sensor element.

It is possible to use a plate made of a metal, synthetic resin, or ceramics capable of securing strength and toughness as contact-bonding means of the present invention. As shown in FIG. 1, it is also possible to use the front-end back protective layer of a flat substrate as contact-bonding means at the same time.

Figure 5:
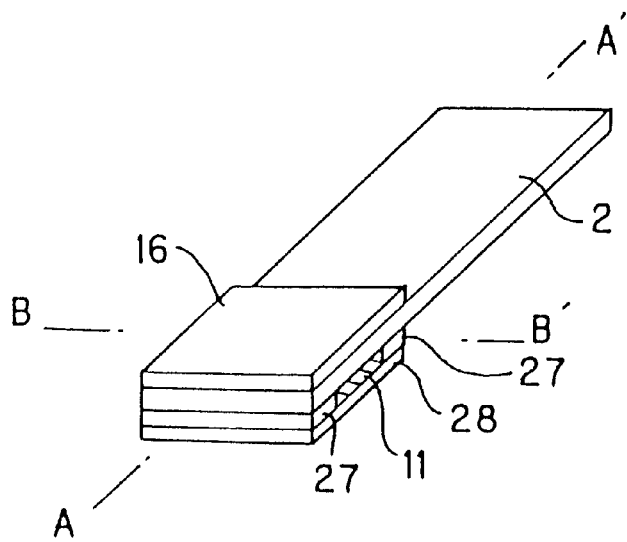
Figure 5:
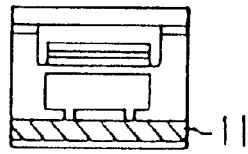
Figure 5:
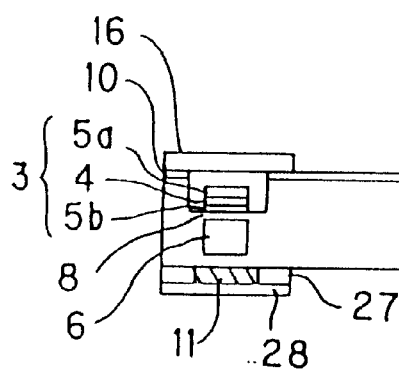
Figure 5:
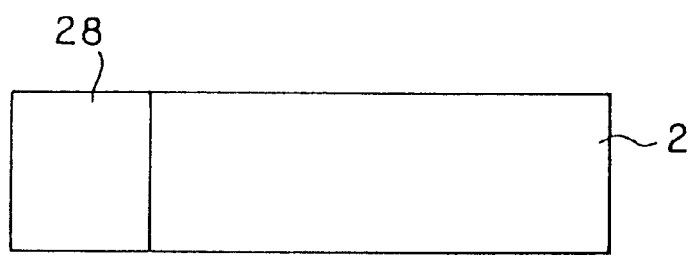

Moreover, a method of contact-bonding a substrate with a porous body is not restricted as long as it meets the relation of $0.1t_0 \leq t < t_0$. As shown in FIG. 5, for example, the following method is considered: a method of mounting a porous body 11 on a substrate 2 and then, superimposing a contact-bonding member 28 on the porous body 11 and fixing a protrusion 27 formed on the substrate 2 with the contact-bonding member 28 by an adhesive or a method of pressing the protrusion 27 and the contact-bonding member 28 by a spring.

It is possible that the shape of a porous body is not restricted as long as the shape is able to cover at least an envelopment space. However, when considering how easily the porous body can be machined, how easily the porous body can be set to a substrate, and how uniformly a pressure is applied to the porous body, it is preferable that the porous body is a flat plate.

Moreover, in the case of the present invention, it is preferable to set the surface roughness of a substrate in at least the contact portion between a porous body and the substrate to 50 $\mu$m or less and it is more preferable to set the surface roughness to 10 $\mu$m or less in order to improve the adhesiveness between the substrate and the porous body by smoothing the surface of the substrate.

However, when setting the surface roughness of the substrate to 50 $\mu$m or more, a trouble may occur that the porous body may be replaced with bubbles similarly to the case in which a gap is produced between the substrate and the porous body.

A method of making a porous body contact with a fluid is not restricted. However, as shown in FIG. 1, it is preferable to make an overhanging portion 12 contact with the fluid by providing the overhanging portion 12 for the porous body Thus, a fluid is not sufficiently present nearby the substrate 2 and the overhanging portion 12 wet by the fluid serves as a buffering portion even when a lot of bubbles are present. Moreover, when using a porous body made of fiber such as a woven fabric, it is possible to sufficiently introduce a fluid by using the capillarity. Therefore, the effect of preventing the replacement of a fluid with bubbles is further improved compared to the case of only setting a porous body.

It is preferable that the overhanging portion 12 overhangs from the substrate 2 by approximately 1 to 10 mm in order to secure the above function.

Figure 6:
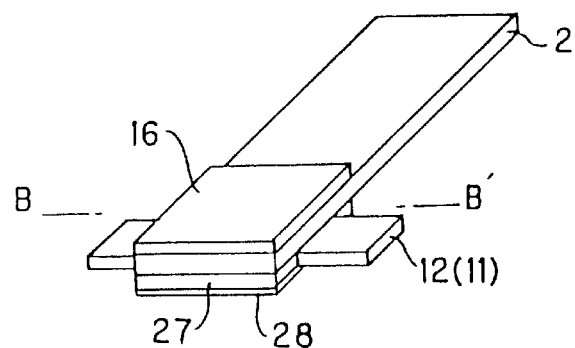
Figure 6:
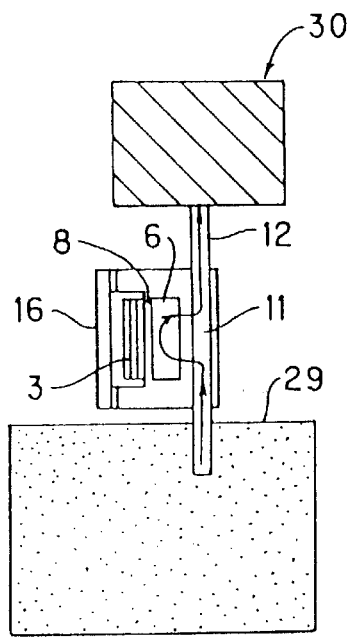
Figure 6:
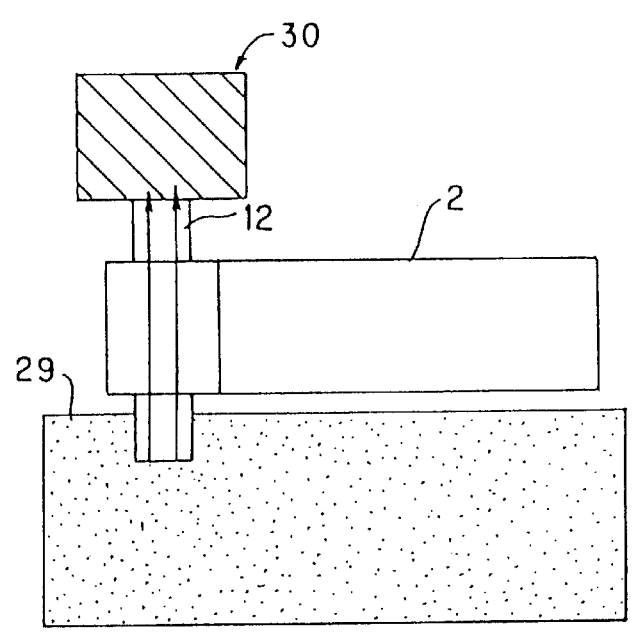

Moreover, as shown in FIGS. 6(a) to 6(c), by forming a structure in which one end of the overhanging portion 12 in its longitudinal direction contacts a fluid 29 and the other end of it contacts a fluid absorbent 30, it is possible to preferably apply the structure to a fluid to be measured whose specific gravities, compositions, and concentrations are relatively quickly changed.

That is, because the fluid 29 quickly flows through a porous body and moreover, through the envelopment space 6 serving as a measurement space, it is possible to completely correspond to the case in which specific gravities, compositions, and viscosities of the fluid 29 are quickly changed.

It is necessary to use a material capable of absorbing the fluid 29 through the capillarity as the fluid absorbent 30. It is also possible to use a woven fabric or non-woven fabric made of an organic or inorganic fiber as the porous body 11 of the present invention. For example, it is possible to preferably use a macromolecular absorbent used for, for example, a paper diaper as the porous body 11.

Figure 7:
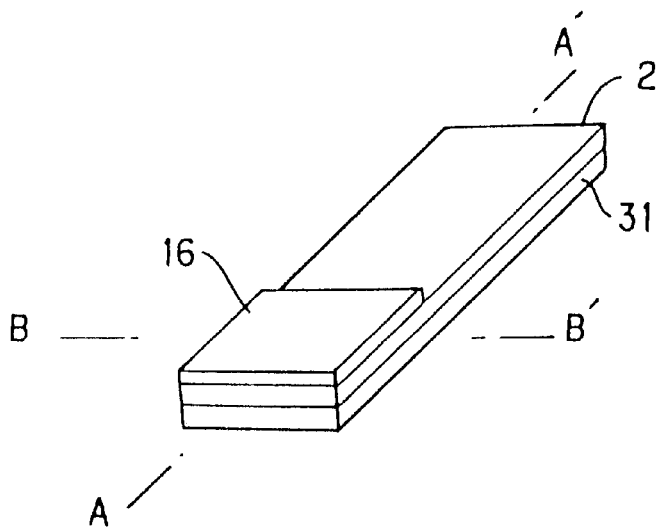
Figure 7:
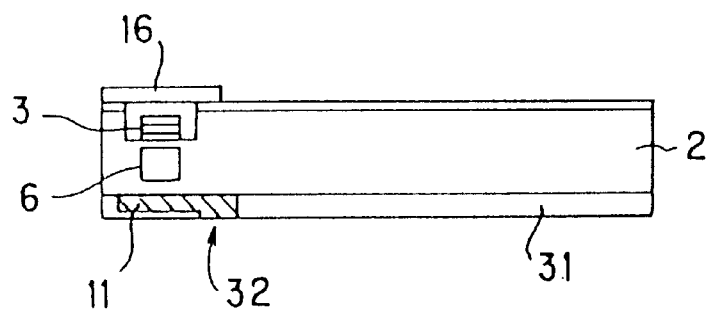
Figure 7:
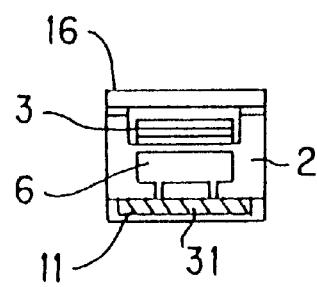
Figure 7:
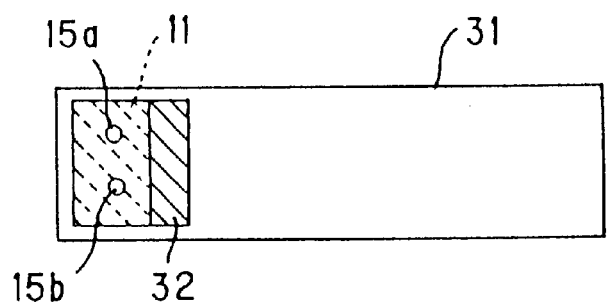

However, when applying the structure to a fluid to be measured whose measurement factors are relatively slowly changed, it is also possible to use a contact method in which the porous body 11 is sealed by contact-bonding means 31 having a window 32 and the porous body 11 face-contacts with the fluid 29 through the window 32 as shown in FIG. 7.

Figure 8:
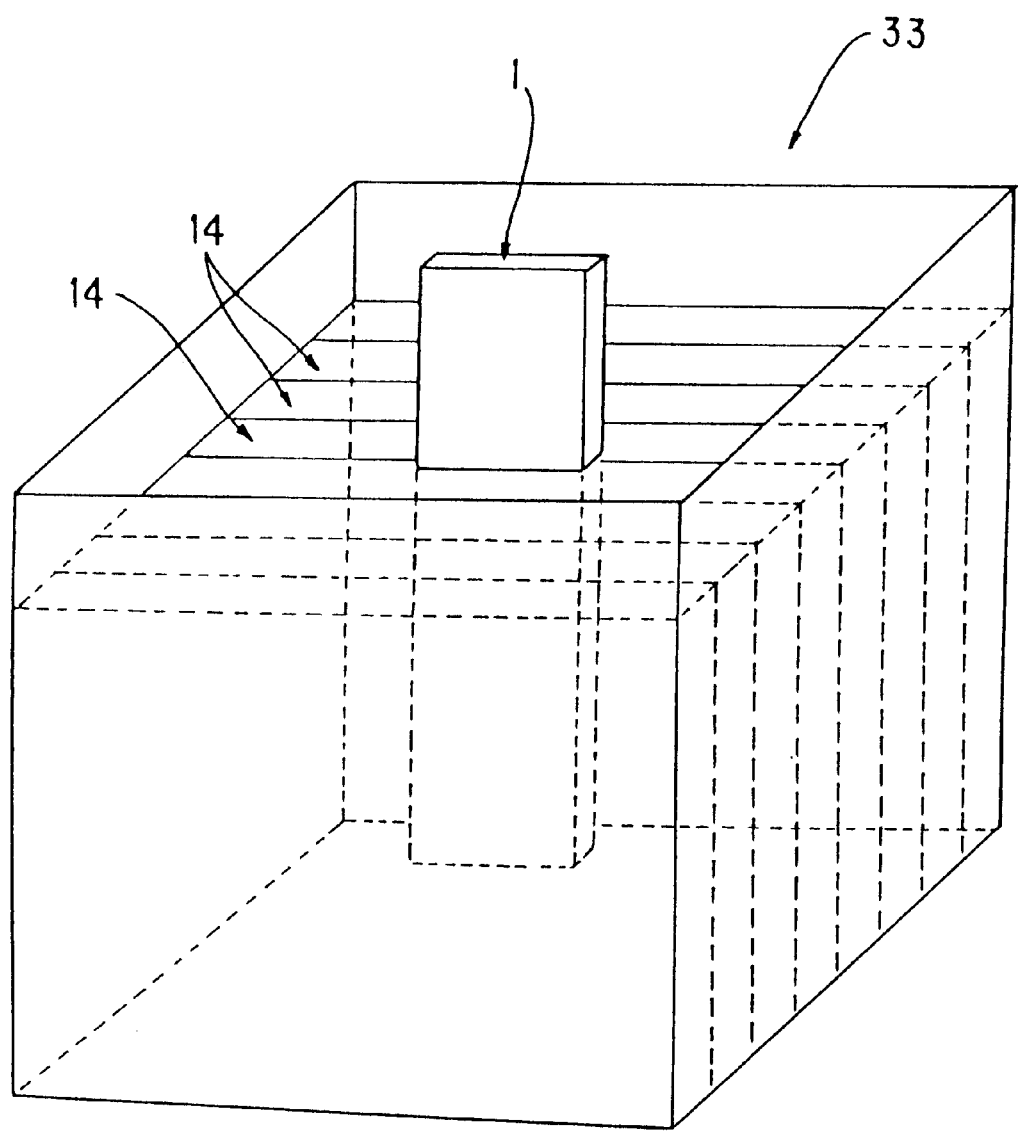
FIG. 8 is a schematic perspective view showing a working state of a sensor

This method, as shown in FIG. 8, can be preferably used to measure the viscosity of an electrolyte permeating the separator 14 inserted between the electrodes of, for example, a lead acid battery 33.

Figure 9:
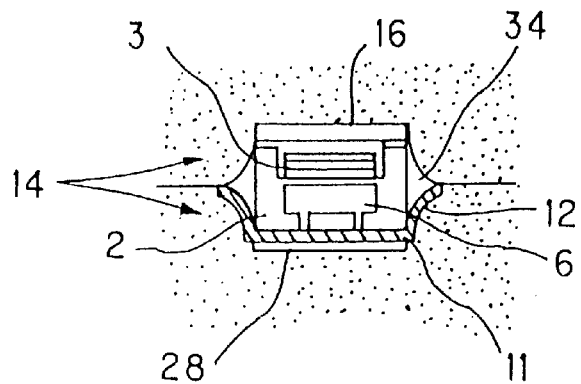
FIGS. 9(a) to 9(c) are sectional views of a sensor element held by a separator.
Figure 9:
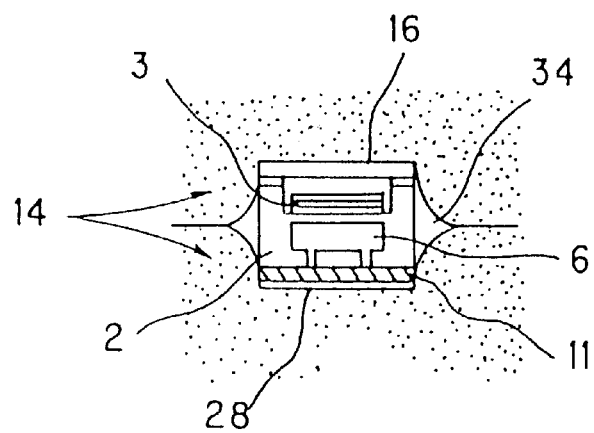
Figure 9:
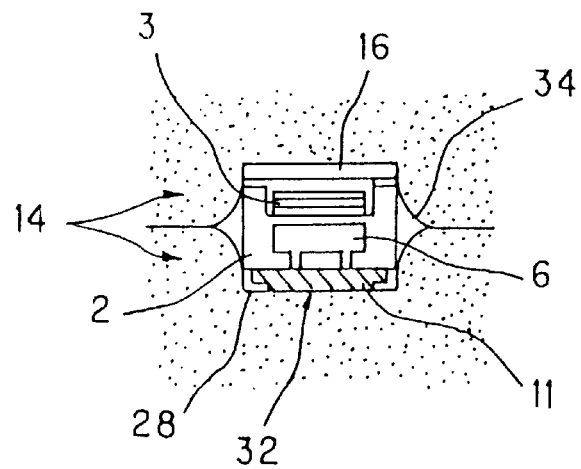
Figure 10:
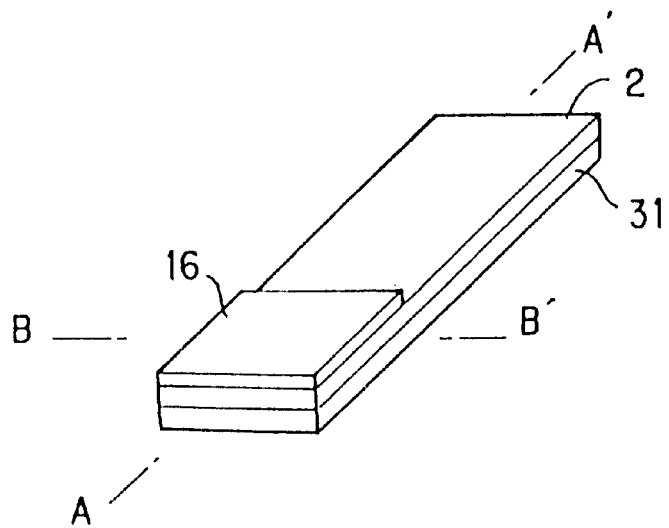
Figure 10:
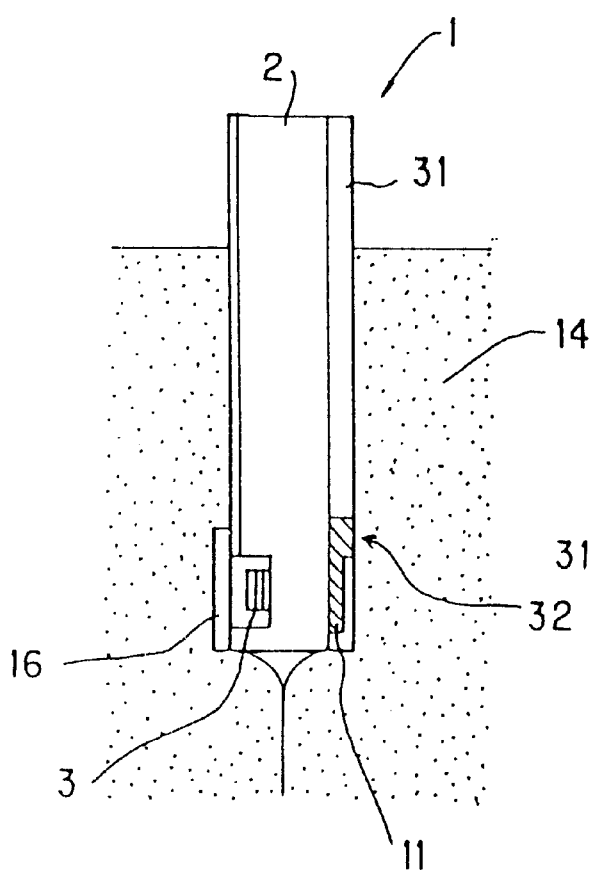
Figure 10:
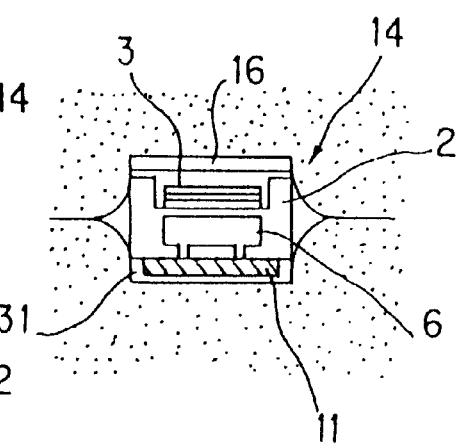

That is, even when the overhanging portion 12 is used, a fluid is easily replaced with air because the overhanging portion 12 contacts a dead space 34 produced between the separator 14 and the substrate 2 as shown in FIG. 9(a). Moreover, as shown in FIG. 9(b), a fluid cannot be sufficiently introduced into the envelopment space 6 only by setting the porous body 11 to the flat substrate 2. However, as shown in FIG. 9(c) and FIG. 10, the structure in FIG. 7 makes it possible to avoid the above trouble because the whole of the window 32 directly face-contacts the separator 14 and it is not influenced by the dead space 34.

The shape of the window 32 is not restricted as long as the window 32 is securely able to press a porous body. However, it is preferable to form a window at a portion other than the portion directly contact-bonding a porous body to a communication hole, that is, contact-bonding means is at least set immediately above the communication hole.

For example, the types of ceramic substrates shown in FIG. 7(d), FIGS. 11(a) to 11(d), and FIG. 12(a) are preferable because the contact-bonding member 31 is present on the communication holes 15a and 15b and a pressure securely works on the holes 15a and 15b and thus, a large effect for preventing a fluid from being replaced with bubbles is obtained.

However, because the type having a window on a communication hole has a short route between an envelopment space and an external space, it quickly responds to the change of measurement factors of the fluid around a sensor element. That is, the type has a quick response.

Figure 12:
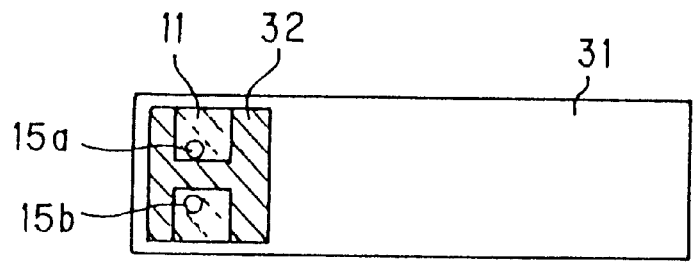
FIGS. 12(a) to 12(c) are bottom views showing still another embodiment of the ceramic substrate of the present invention in FIGS. 10(a) to 10(c).
Figure 12:
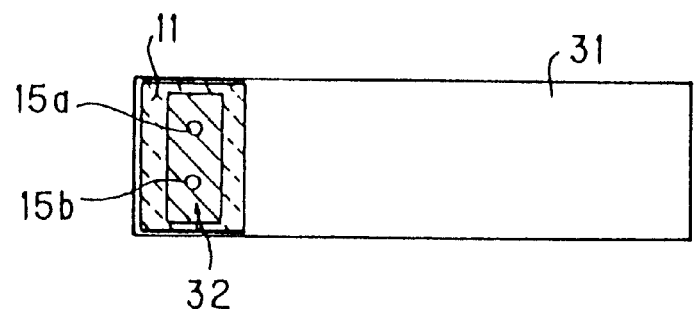
Figure 12:
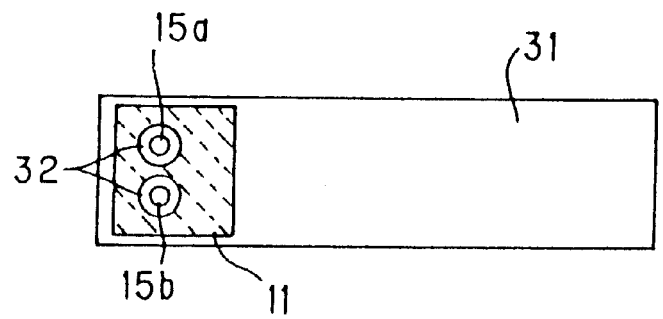

From this viewpoint, the types in FIGS. 12(b) and 12(c) are preferable. From the viewpoint of a large contact area with a fluid, the type in FIG. 12(b) is more preferable.

Moreover, the type having a lot of windows or a large window area also has a quick response.

Figure 11:
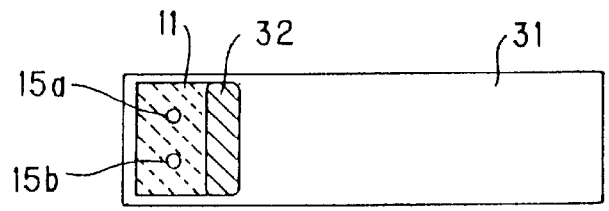
FIGS. 11(a) to 11(d) are bottom views showing another embodiment of the ceramic substrate of the present invention in FIGS. 10(a) to 10(c).
Figure 11:
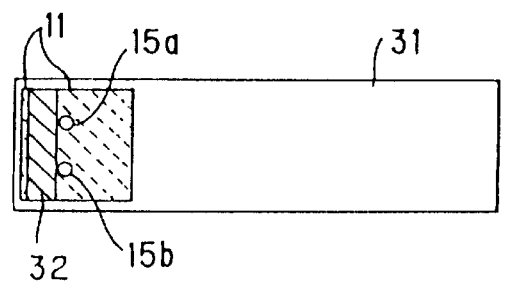
Figure 11:
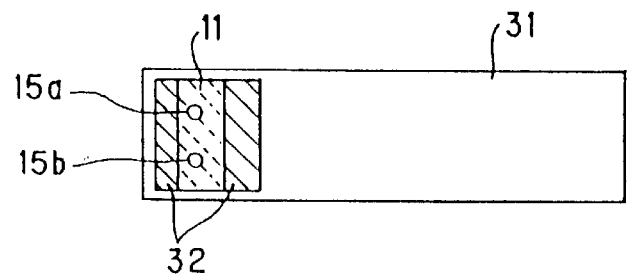
Figure 11:
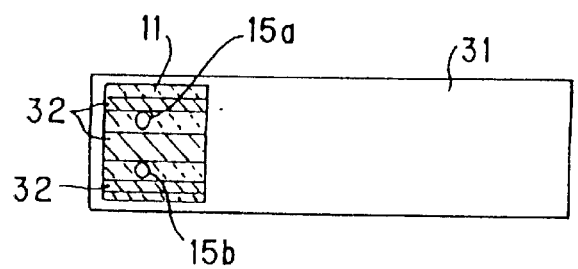

From this viewpoint, the types in FIGS. 11(c) and 11(d), and FIG. 12(b) are preferable.

Therefore, from the viewpoints of the position and shape of a window, the types in FIGS. 11(c) and 11(d) are preferable as the result of synthetically judging the above features.

Figure 13:
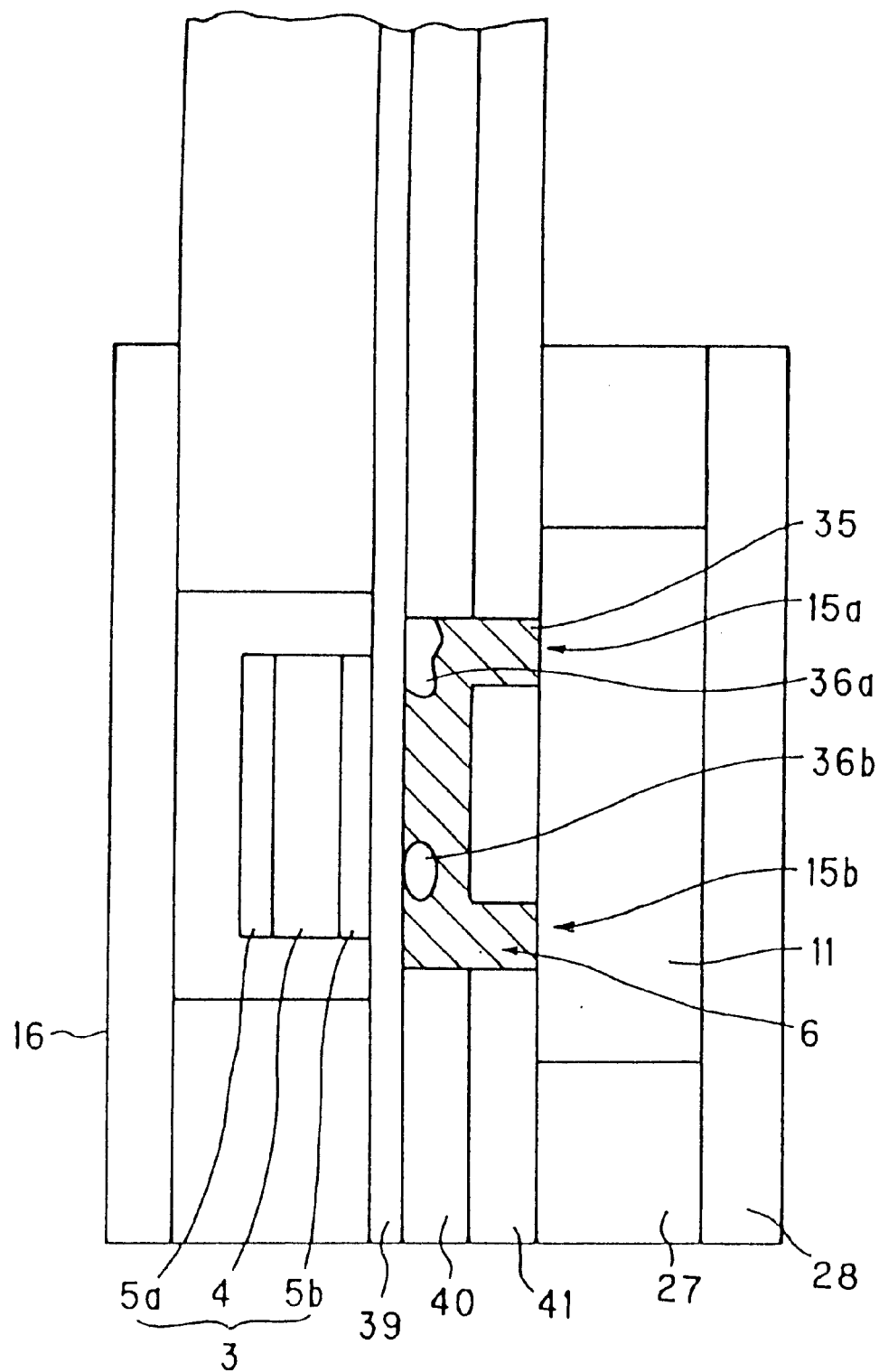
FIG. 13 is a sectional illustration showing an embodiment of a sensor element of the present invention.

A sensor element of the present invention is characterized by using a ceramic substrate of the present invention. Therefore, it is preferable to fill the envelopment space 6, communication holes 15a and 15b, and the hole on a porous body with any one 35 of a solid soluble in a fluid, a high-viscosity liquid soluble in a fluid, a solid reactive on a fluid, and a high-viscosity liquid reactive on a fluid in order to easily introduce a fluid to be measured into the envelopment space of a flat substrate constituting the ceramic substrate as shown in FIG. 13. Moreover, it is preferable that any one 35 of a solid soluble in a fluid, a high-viscosity liquid soluble in a fluid, a solid reactive on a fluid, and a high-viscosity liquid reactive on a fluid is replaced with a fluid.

Moreover, it is permitted that a part of the envelopment space, communication holes, and the hole of the porous body is filled with the one of the above continuously or discontinuously.

When a "solid or high-viscosity liquid soluble in a fluid" dissolves in the fluid, the fluid replaces the solid or high-viscosity liquid and thereby, it more easily fills the envelopment space. Moreover, when a "solid or high-viscosity liquid reactive on a fluid" reacts on the fluid, the fluid replaces the solid or high-viscosity liquid and thereby, it more easily fills the envelopment space.

In this case, the "solid" can be a powdery or granular material, paste, or poly-crystalline lump.

In the case of a "solid soluble in a fluid", it is preferable that the solubility to 100 g of the fluid is 0.01 g or more at 25° C. or an operating temperature at which a sensor element can operate. However, it is preferable that the solubility is 0.1 g or more, it is more preferable that the solubility is 0.5 g or more and it is particularly preferable that the solubility is 1 g or more. This is because the fluid more easily dissolves the solid and more easily enters the envelopment space when the solid has a higher solubility.

For example, when the fluid is water, salts such as sodium chloride {solubility: 35.9 g (25° C.)}, potassium chloride {solubility: 35.9 g (25° C.)}, and sodium bromide and saccharides such as glucose and sucrose are listed.

Moreover, when the fluid is an acid such as sulfuric acid or hydrochloric acid, it is preferable to use a salt comprising a weak acid and strong base in general. For example, it is possible to preferably use sodium bicarbonate, sodium carbonate, or calcium carbonate because it has a high solubility.

Furthermore, when the fluid is a base such as a sodium-hydroxide aqueous solution or potassium-hydroxide aqueous solution, it is preferable to use a salt comprising a strong acid and weak base. For example, it is possible to preferably use ammonium chloride or ammonium sulfate because it has a high solubility.

A "solid soluble in a fluid" may duplicate with a "solid reactive on a fluid". For example, when the fluid is an acid such as sulfuric acid and the solid soluble in the fluid is a "salt comprising a weak acid and strong base" such as sodium bicarbonate, the solid reacts on and dissolves in the fluid because it is neutralized.

As a "solid reactive on a fluid", a salt causing the above neutralization with the fluid and a substance causing hydrolysis when the fluid is water are listed. For example, alkali alkoxide such as sodium methoxide is listed.

It is preferable that a "solid soluble in a fluid" or "solid reactive on a fluid" does not include any blow hole.

For example, in the case of the flat substrate shown in FIG. 13, the gas in the blow hole is not exhausted or replaced with the fluid when one communication hole 15b is present in a fluid but the other communication hole 15a is open to the atmosphere or unless the gas in the blow hole is a "gas soluble in a fluid".

Therefore, as long as the accuracy of a sensor is not influenced, it is permitted that blow holes 36a and 36b are present. However, when manufacturing a flat substrate by filling an envelopment space with a solution obtained by dissolving a "solid soluble in a fluid" or a solvent obtained by dispersing a "solid reactive on a fluid" and thereafter removing the solvent and replenishing the solid, it is preferable to manufacture the flat substrate so that the number of blow holes is minimized.

A "high-viscosity liquid soluble in a fluid" and a "high-viscosity liquid reactive on a fluid" can be used similarly to the solid. A high-viscosity liquid is superior and preferable from the viewpoint that it can be easily introduced into an envelopment space and porous body compared to a solid.

The "high-viscosity liquid soluble in a fluid" can use a monosaccharide, saccharide, or a mixture of them, or a mixture with gum arabic.

A method for manufacturing a sensor element of the present invention is described below.

Figure 14:
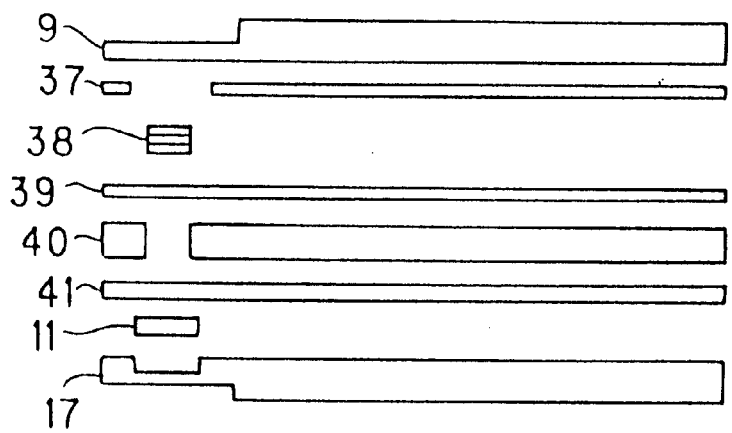
FIG. 14 is a sectional illustration showing a method for manufacturing a sensor element of the present invention.

Fig. 14 is a lateral sectional view showing the method for manufacturing a sensor element of the present invention shown in FIG. 1.

In FIG. 14, symbol 9 denotes a piezoelectric-element protection layer, 37 denotes a bonding layer (10 in FIGS. 1 and 5), 38 denotes a piezoelectric element layer, 39 denotes a vibrational portion layer, 40 denotes an envelopment space forming layer, 41 denotes a communication hole layer, 11 denotes a porous body, and 17 denotes a front-end back protective layer.

First, the vibrational portion layer 39, envelopment space forming layer 40, and communication hole layer 41 are green-sheet-superimposed and fired. Then, the piezoelectric element layer 38 is formed and thereafter, glass paste is screenprinted to form the bonding layer 37. Finally, the piezoelectric element protection layer 9 is fusion-bonded with glass to solidify the front-end back protective layer 17 with an adhesive so as to hold the porous body 11.

Figure 15:
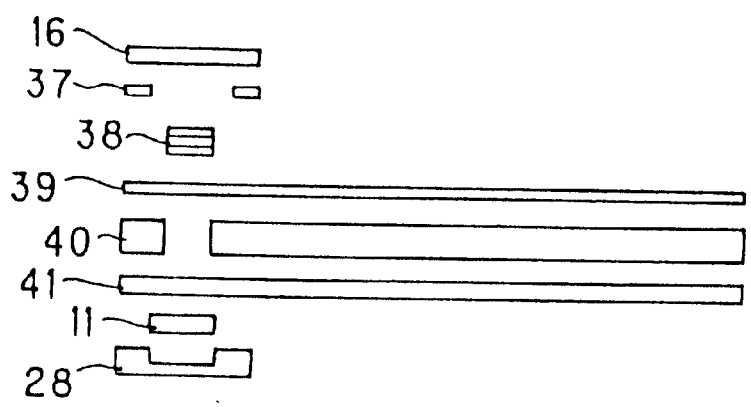
FIG. 15 is a sectional illustration showing another method for manufacturing a sensor element of the present invention.

As shown in FIG. 15, the piezoelectric element protective layer 9 can be replaced with a cover 16 capable of protecting at least a piezoelectric element and the front-end back protective layer 17 can be replaced with a contact-bonding member 28 capable of holding at least a porous body.

As described above, it is possible to manufacture the sensor element 1 having a ceramic substrate obtained by contact-bonding the porous body 11 having flexibility by the pressure in the laminate direction with the flat substrate 2.

The sensor element 1, as shown in FIGS. 8 and 10(b), is set in a lead acid battery and used by being held so as to be embedded in the porous separator 14 held between a pair of electrodes of the battery.

In the case of a ceramic substrate and a sensor element of the present invention using the ceramic substrate, a gap is not easily produced between a flat substrate and a porous body differently from the case of only contacting the porous body with the flat substrate. Therefore, even when a fluid is not sufficiently present nearby a substrate or there are a lot of bubbles, it is possible to prevent the fluid in an envelopment space from being replaced with bubbles again.

What is claimed is:

1. A ceramic substrate comprising:
    a flat ceramic substrate in which an envelopment space is formed;
    a porous body disposed so as to cover said envelopment space, said porous body having flexibility and providing a fluid communication path, by virtue of wettability, between said envelope space and the exterior of said flat ceramic substrate; and
    contact-bonding means for contact-bonding said porous body to said flat ceramic substrate in the laminate direction, wherein at least a portion of said porous body is sandwiched between at least a portion of said flat ceramic substrate and at least a portion of said contact-bonding means.

2. The ceramic substrate according to claim 1, wherein the relation between a thickness t of the porous body contact-bonded by the contact-bonding means with the flat ceramic substrate in the laminate direction and a thickness $t_0$ of the porous body before contact-bonded meets the following expression (1):

$$0.1t_0 \leq t < t_0 \qquad (1).$$

3. The ceramic substrate according to claim 1, wherein the porous body comprises a woven fabric or non-woven fabric made of any one of natural fiber, synthetic fiber, and inorganic fiber.

4. The ceramic substrate according to claim 1, wherein
    the envelopment space communicates with the exterior through at least two communication holes is formed in the flat ceramic substrate, and
    the porous body is disposed so as to cover all of said communication holes.

5. The ceramic substrate according to claim 4, wherein the contact-bonding means has a window for making the porous body face-contact with a fluid and the porous body is sealed by the contact-bonding means.

6. The ceramic substrate according to claim 5, wherein the window is formed on a portion of the contact-bonding means other than the portion thereof used for directly contact-bonding the porous body to the flat ceramic substrate.

7. The ceramic substrate according to claim 1, wherein the porous body has an overhanging portion to the outside of the flat ceramic substrate.

8. The ceramic substrate according to claim 7, wherein one end of the overhanging portion in the longitudinal direction contacts a fluid and the other end of the portion contacts a fluid absorbent.

9. The ceramic substrate according to claim 1, wherein the flat ceramic substrate in at least the portion of it contacting the porous body has a surface roughness of 50 μm or less.

10. A sensor element comprising:
    a flat ceramic substrate in which an envelopment space is formed at least in part by a first major surface of a vibrational portion;
    a porous body disposed so as to cover said envelopment space, said porous body having flexibility and providing a fluid communication path, by virtue of wettability, between said envelope space and the exterior of said flat ceramic substrate;
    contact-bonding means for contact-bonding said porous body to said flat ceramic substrate in the laminate direction, wherein at least a portion of said porous body is sandwiched between at least a portion of said flat ceramic substrate and at least a portion of said contact-bonding means; and
    a piezoelectric element secured to a second, opposed major surface of said vibrational portion such that said piezoelectric element is separated from said envelope space by said vibrational portion, said piezoelectric element comprising a piezoelectric film and a pair of electrodes contacting said piezoelectric film.

11. The sensor element according to claim 10, wherein said envelopment space and interstices of said porous body are filled with at least one member selected from the group consisting of a solid soluble in a fluid, a high-viscosity liquid soluble in a fluid, a solid reactive with a fluid, and a high-viscosity liquid reactive with a fluid.

12. The sensor element according to claim 11, wherein said member is one capable of being replaced with a fluid.

* * * * *